(12) United States Patent
Lee et al.

(10) Patent No.: US 11,819,477 B2
(45) Date of Patent: Nov. 21, 2023

(54) NANOPARTICLES FOR SELECTIVE DEATH OF CANCER CELLS THROUGH FERROPTOSIS, METHOD OF PREPARING THE SAME, AND USE OF THE NANOPARTICLES

(71) Applicant: SEOUL NATIONAL UNIVERSITY R & DB FOUNDATION, Seoul (KR)

(72) Inventors: Kang Won Lee, Suwon-si (KR); Chae Won Bae, Suwon-si (KR); Min Hee Park, Cheongju-si (KR)

(73) Assignee: SEOUL NATIONAL UNIVERSITY R & DB FOUNDATION, Seoul (KR)

( * ) Notice: Subject to any disclaimer, the term of this patent is extended or adjusted under 35 U.S.C. 154(b) by 0 days.

(21) Appl. No.: 16/727,314

(22) Filed: Dec. 26, 2019

(65) Prior Publication Data

US 2020/0261498 A1    Aug. 20, 2020

(30) Foreign Application Priority Data

Dec. 26, 2018   (KR) ........................ 10-2018-0169916
Mar. 8, 2019    (KR) ........................ 10-2019-0026617

(51) Int. Cl.
| | | |
|---|---|---|
| A61K 33/26 | (2006.01) | |
| A61K 47/69 | (2017.01) | |
| A61P 35/00 | (2006.01) | |
| A61K 9/14 | (2006.01) | |
| C08J 3/075 | (2006.01) | |

(Continued)

(52) U.S. Cl.
CPC ............... *A61K 33/26* (2013.01); *A61K 9/14* (2013.01); *A61K 47/06* (2013.01); *A61K 47/6903* (2017.08); *C08J 3/075* (2013.01); *A61P 35/00* (2018.01)

(58) Field of Classification Search
CPC .... A61K 33/26; A61K 47/61; A61K 47/6903; A61K 9/14; A61P 35/00; C08J 3/075
See application file for complete search history.

(56) References Cited

U.S. PATENT DOCUMENTS

2009/0110644 A1 * 4/2009 Margel ................... A61P 29/00
                                                             424/9.42
2017/0143756 A1 * 5/2017 Smejkalova ........... A61K 33/30

FOREIGN PATENT DOCUMENTS

KR        10-1624842 B1    5/2016
KR    10-2017-0021351 A    2/2017

OTHER PUBLICATIONS

Li et al., Multifunctional smart hydrogels: potential in tissue engineering and cancer therapy, Apr. 2018, Journal of Materials Chemistry B, 6, 4714-4730 (Year: 2018).*

(Continued)

*Primary Examiner* — Bethany P Barham
*Assistant Examiner* — Ayaan A Alam
(74) *Attorney, Agent, or Firm* — Vorys, Sater, Seymour and Pease LLP; Mih Suhn Koh

(57) ABSTRACT

Provided are nanoparticles for the selective death of cancer cells through ferroptosis and a method of preparing the same. More particularly, the nanoparticles are in a form in which a cancer cell-targeting hydrogel and iron particles are bound and aggregated, and are selectively accumulated in cancer cells, and thus exhibit an effective cancer cell killing effect through ferroptosis, and accordingly, are expected to exhibit high therapeutic effects due to less side effects.

5 Claims, 19 Drawing Sheets

Specification includes a Sequence Listing.

(51) Int. Cl.
  *A61K 47/06* (2006.01)
  *A61K 47/61* (2017.01)

(56) References Cited

OTHER PUBLICATIONS

Gaumet et al., Nanoparticles for drug delivery: The need for precision in reporting particle size parameters, 2008, European Journal of Pharmaceutics and Biopharmaceutics, 69, 1-9 (Year: 2008).*

Li, J. et al., "Hyaluronic Acid-modified Fe3O4@Au core/shell nanostars for multimodal imaging and photothermal therapy of tumors", 2015, Biomaterials, 38, 10-21 (Year: 2015).*

Pamfil, D., Nanogels of Natural Polymers, Feb. 2018, Department of Physical chemistry of polymers, "Petru Poni" Institute of Macromolecular Chemistry of Romanian Academy, Chapter 4, 71-110 (Year: 2018).*

Zhang et al., "Thermosensitive/superparamagnetic iron oxide nanoparticle-loaded nanocapsule hydrogels for multiple cancer hyperthermia", 2016, Elsevier, Biomaterials 106, 13-23 (Year: 2016).*

Bae et al., "Molecular regulation of ferroptotic cancer cell death by fabrication of functionalized iron nanoparticles" in 2018 Symposium of The Korean Society for Biomaterials, published on Mar. 29, 2018, 2 pages.

Bae et al., "Fabrication of functionalized iron nanoparticles for molecular regulation of ferroptotic cancer cell death" in Nano Korea 2018, published on Jul. 10, 2018, 2 pages.

Bae et al., "Regulation of ferroptotic cancer cell death by fabrication of functionalized iron nanoparticles" in 2018 International Symposium on New Frontiers in Nono-Bio-Electronic Convergence Science and Technology, published on Dec. 3, 2018, 2 pages.

Zheng et al., "Switching Apoptosis to Ferroptosis: Metal-Organic Network for High-Efficiency Anticancer Therapy", Nano Letters, 2017, vol. 17, pp. 284-291.

* cited by examiner

NANOPARTICLES FOR SELECTIVE DEATH OF CANCER CELLS THROUGH FERROPTOSIS, METHOD OF PREPARING THE SAME, AND USE OF THE NANOPARTICLES

CROSS-REFERENCE TO RELATED APPLICATION

This application claims priority to and the benefit of Korean Patent Application No. 10-2018-0169916, filed on Dec. 26, 2018, and No. 10-2019-0026617, filed on Mar. 8, 2019, the disclosure of which is incorporated herein by reference in its entirety.

SEQUENCE LISTING

The Sequence Listing submitted in text format (.txt) filed on Dec. 26, 2019, named "SequenceListing.txt", created on Dec. 20, 2019 (1.64 KB), is incorporated herein by reference.

BACKGROUND

1. Field

The present disclosure relates to nanoparticles for the selective killing of cancer cells through ferroptosis, a method of preparing the same, and a use of the nanoparticles.

2. Discussion of Related Art

Most existing anticancer drugs generally act on various metabolic pathways of cells being actively dividing and inhibit the synthesis of nucleic acids or exhibit cytotoxicity, thereby exhibiting anticancer activity, and thus damage even normal cells, especially cells of tissue in which cell division actively occurs, rather than selectively acting only on cancer cells, and consequently have a serious limitation of causing side effects such as vomiting, gastrointestinal disorders, alopecia, and leukopenia due to myelosuppression.

Therefore, to overcome this limitation, research on target therapy for selecting and attacking cancer cells among normal cells has been actively conducted. Targeted therapeutic agents selectively attack cancer cells by targeting specific biological substances such as vascular endothelial growth factor (VEGF), epidermal growth factor (EGF), and mutated receptors, and thus may reduce damage to normal cells. However, these targeted therapies also have limitations. First, since such agents target specific biomaterials, even patients diagnosed with the same cancer do not have a therapeutic effect if they do not have specific biomaterials. For example, gefitinib exhibits a therapeutic effect only in some patients with non-small cell lung cancer, but it has been discovered that, since gefitinib targets epidermal growth factor receptor (EGFR) mutations, only patients with mutated non-small cell lung cancer exhibit therapeutic effects. In addition, such targeted therapeutic agents have problems such as a significant reduction in therapeutic effects due to the fact that, when continuously used, cancer cells have resistance thereto.

Therefore, in recent years, interest in nanomedicine using nanomaterials, which is a new method, has been increasing. Nanomedicine is a technology that combines nano-sized materials with medicine, and can be applied to various fields such as nanobiosensors, nanoimaging, nanopharmaceutical carriers, and nanotissue engineering, and thus is expected to be a breakthrough technology that can overcome the challenges of diagnosis and treatment of intractable diseases such as cancer, dementia, and cardiovascular disease. In the United States, the federal government has established the nanotechnology development strategy since 1998 and launched the National Nanotechnology Initiative (NNI) in which 12 federal agencies participate, and is investing more than 1 billion dollars annually. Recently, diagnostic kits and therapeutic agents using nanoparticles have entered clinical trials or have been approved by the US Food and Drug Administration, and research on nanomedicine is actively conducted. In Korea, the 2002 Nano Technology Development Promotion Act was enacted, and investment is continuously made every year according to the Nanotechnology Integrated Development Plan. Attempts have been made to use nanoparticles for cancer treatment, and since these nanoparticles mostly affect normal cells, they may cause various side effects. To improve this, methods for aiming at specific targets, such as passive targeting and active targeting, have been studied, but the development of nanoparticles that exhibit less side effects and high therapeutic effects, which can be substantially used for cancer treatment, is still inadequate.

Meanwhile, ferroptosis is a cell death method by iron-mediated lipid peroxidation, in which iron meets the reactive oxygen species (ROS) to induce the Fenton reaction, resulting in accumulation of lipid peroxides in cells, causing cell death. Recently, research on a method of killing cancer cells using such ferroptosis has been reported ("Nano Lett. (2017) 17(1): 284-291"). More specifically, by using nanoparticles in which a plasmid expressing p53 that regulates oxidative stress is bound to a metal-organic network that induces a Fenton reaction, cancer cell death is induced through the ferroptosis/apoptosis hybrid pathway, and polyethyleneimine (PEI) used in the nanoparticles, which is a cationic polymer, is widely used as a gene carrier, but is not substantially suitable for use in cancer treatment due to cytotoxicity thereof.

Therefore, the inventors of the present disclosure had conducted intensive studies on nanoparticles which can be effectively used for the treatment of various cancers, have low cytotoxicity, and are capable of inducing cell death through cancer cell-specific ferroptosis, and thus completed the present disclosure.

CITED REFERENCES

Non-Patent Document (Non-Patent Document 1) Nano Lett. (2017) 17 (1): 284-291

SUMMARY

Provided are nanoparticles which can be effectively used for the treatment of various cancers, have low cytotoxicity, and are capable of inducing cell death through cancer cell-specific ferroptosis, a method of preparing the nanoparticles, a use of the nanoparticles, and the like.

However, the technical problem to be achieved by the present disclosure is not limited to the above-mentioned problem, and other unmentioned technical problems may be clearly understood by those skilled in the art to which the present disclosure pertains from the following description.

Unless defined otherwise, all technical terms used herein have the same meaning as is commonly understood by one of ordinary skill in the art to which the present disclosure pertains. In addition, although exemplary methods or samples are described in the present specification, those similar or equivalent thereto also fall within the scope of the present disclosure. In addition, numerical values described in the present specification are considered to include the meaning of "about" unless stated otherwise. In the present specification, when a portion is referred to as "including" or "comprising" an element, unless otherwise specifically stated, this does not preclude other elements and also may mean that other elements are further included. The disclosures of the cited references are incorporated herein by reference in their entirety.

The present disclosure provides a pharmaceutical composition for the prevention or treatment of cancer including, as an active ingredient, nanoparticles including an iron and a cancer cell-targeting hydrogel.

In one embodiment of the present disclosure, the nanoparticles may be in a form in which an iron cation and an anion of a cancer cell-targeting hydrogel are bound and aggregated, and may be nanoparticles obtained by a method for co-precipitation of a hydrogel and an iron ion without addition of an additional linker, surfactant, compound, or the like, i.e., obtained by adding an iron to a hydrogel solution and stirring the resulting solution to co-precipitate a hydrogel and the iron, or may also be nanoparticles obtained by a pre-gel method in which a nano-sized conjugate dispersed in a water continuous phase is formed by stirring a hydrogel and an iron. The anion of the cancer cell-targeting hydrogel may be a carboxyl group, but is not limited as long as it is an anion functional group in a form capable of secondarily binding to the iron ion. The iron ion is a vital substance for cell survival involved in oxygen transportation, DNA biosynthesis, ATP synthesis, and the like, and may also generate reactive oxygen species along with ATP synthesis in mitochondria.

In another embodiment of the present disclosure, the iron in the aggregated form may be preferably iron ion, binding form of iron ion and oxygen, binding form of iron ion and the hydrogel or iron oxide, which is a compound of iron and oxygen, more preferably $Fe_3O_4$, but the present disclosure is not limited thereto.

In another embodiment of the present disclosure, the cancer cell-targeting hydrogel refers collectively to any hydrogel capable of selectively binding to a molecule, a receptor, or the like expressed on surfaces of cancer cells, and the cancer cell-targeting hydrogel may be any hydrogel known in the art which is selectively binding to a molecule or a receptor overexpressed on surfaces of cancer cells, such as CD44, ESA, HER-2/neu, KRAS, an estrogen receptor (ER), or the like, or any cancer cell-targeting hydrogel that can be found in the future. In addition, the cancer cell-targeting hydrogel refer collectively to any hydrogel capable of secondary bonding with iron ions because of carboxylic acids, carboxyl anions, or anions of hydrogel. The hydrogel may be, preferably, hyaluronic acid, carboxymethyl cellulose (CMC), alginates, carboxycellulose, chitosan, collagen, gelatin, or the like, and is, more preferably, hyaluronic acid or derivatives thereof. Hyaluronic acid is biodegradable and highly biocompatible, and is a bio-derived polymer that does not cause an immune response as one of biomaterials. Hyaluronic acid consists of repeating units of glucuronic acid and N-acetylglucosamine which are present not only in the matrix of connective tissues such as lubricating fluids, cartilages, and subcutaneous tissues of the joints but also in the extracellular matrix, umbilical cord, and the vitreous of the eyeball, and is present on cell surfaces of almost all tissues and organs except for red blood cells. In addition, hyaluronic acid has a receptor of CD44 overexpressed on the surface of cancer cells, and thus is suitable for targeting cancer cells.

In another embodiment of the present disclosure, the nanoparticles may preferably have a diameter of 50 nm to 200 nm, but the present disclosure is not limited thereto as long as the nanoparticles are capable of moving into cancer cells.

In another embodiment of the present disclosure, the nanoparticles may induce cancer cell death through ferroptosis, and may also induce ferroptosis by being accumulated in cancer cells to thereby increase the concentration of iron ions in cancer cells. Ferroptosis is a form of iron-dependent cell death, i.e., in-vivo cell death dependent on iron, and may refer to cell death caused by the generation of iron-dependent reactive oxygen species and the generation and accumulation of lipid peroxides.

In another embodiment of the present disclosure, the cancer may preferably be breast cancer, colorectal cancer, rectal cancer, lung cancer, colon cancer, thyroid cancer, oral cancer, pharyngeal cancer, laryngeal cancer, cervical cancer, brain cancer, ovarian cancer, bladder cancer, kidney cancer, liver cancer, pancreatic cancer, prostate cancer, skin cancer, tongue cancer, uterine cancer, gastric cancer, bone cancer, blood cancer, or the like, but the present disclosure is not limited thereto as long as the cancer is any type of cancer that can be recognized by the cancer cell-targeting hydrogel.

The present disclosure also provides a method of preparing nanoparticles including an iron ion and a cancer cell-targeting hydrogel, including: (a) preparing a hydrogel solution by dissolving a cancer cell-targeting hydrogel; and (b) adding an iron ion to the hydrogel solution and stirring the resulting solution.

In one embodiment of the present disclosure, process (b) may be performed by preferably, a co-precipitation method or a pre-gel method, and more preferably, may be performed by sequentially adding an aqueous $FeCl_2 \cdot 4H_2O$ solution while stirring and adding an aqueous $FeCl_3 \cdot 6H_2O$ solution while stirring, but the present disclosure is not limited thereto as long as the method is a method that enables a hydrogel and an iron ion to form a conjugate without addition of an additional linker, compound, surfactant, or the like.

In another embodiment of the present disclosure, the method may further include separating and purifying the nanoparticles prepared after process (b), wherein the separation of the nanoparticles may be performed using a strong neodymium magnet, and the purification of the nanoparticles is not limited as long as it is a general method for purifying nanoparticles, such as sonication, dialysis, or the like.

In another embodiment of the present disclosure, the method may further include dispersing the separated nanoparticles in a solvent.

The present disclosure also provides a method of treating cancer including administering a composition including, as an active ingredient, nanoparticles including an iron and a cancer cell-targeting hydrogel to an individual.

The present disclosure also provides a use of a composition including, as an active ingredient, nanoparticles including an iron ion and a cancer cell-targeting hydrogel for the prevention or treatment of cancer.

Advantageous Effects of Invention

Iron/hydrogel nanoparticles according to the present invention can be used stably without toxicity because it is prepared using only iron and hydrogel particles without additional components as harmless components contained in the body. As the iron/hydrogel nanoparticles of the present invention can be manufactured by an easy method, not only mass production is possible, but also have a high stability, so that it can be stably stored without prolonged aggregation and is a pharmaceutical preparation excellent. In addition, the iron/hydrogel nanoparticles of the present invention specifically accumulate in cancer cells in cancer tissues, and the nanoparticles accumulated inside cancer cells effectively induce cancer cell death through ferroptosis and thus have low side effects in the treatment of various cancers. It is expected to have a high therapeutic effect.

BRIEF DESCRIPTION OF THE DRAWINGS

The above and other objects, features and advantages of the present disclosure will become more apparent to those of ordinary skill in the art by describing in detail exemplary embodiments particular with reference to the accompanying drawings, in which.

DETAILED DESCRIPTION OF EXEMPLARY EMBODIMENTS

Figure 1A:
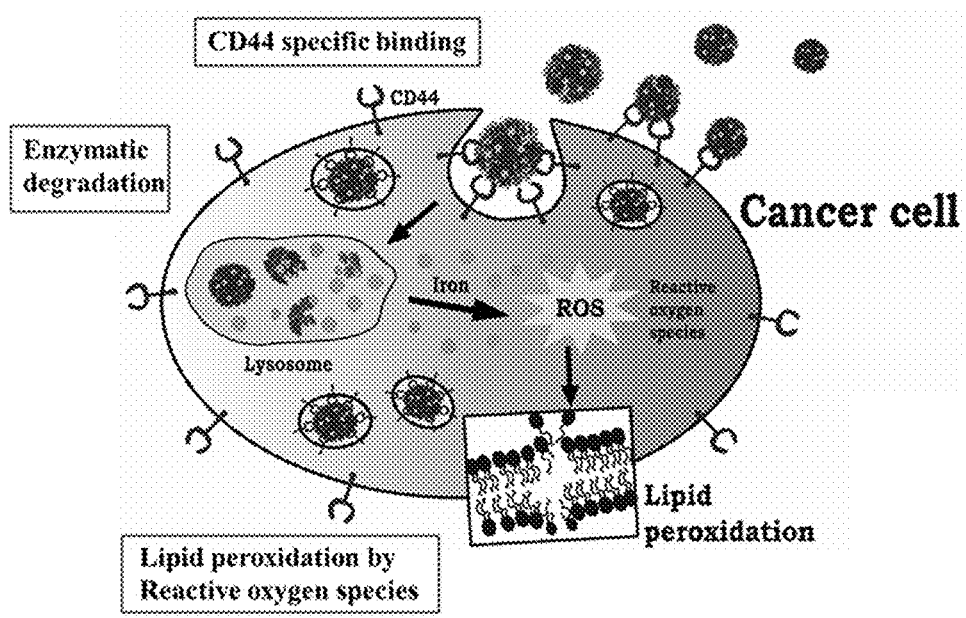
FIG. 1A is a schematic view illustrating a mechanism of iron/hyaluronic acid nanoparticles.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects.

As a result of having conducted intensive studies on nanoparticles exhibiting low toxicity in normal cells and inducing cell death through cancer cell-specific ferroptosis, the inventors of the present disclosure confirmed that nanoparticles consisting of iron particles and a hydrogel are specifically delivered to increase the concentration of iron ion inside a cancer cell, thereby exhibiting a cancer cell killing effect through ferroptosis.

The term "prevention" as used herein means all actions that inhibit diseases such as cancer or delay the onset thereof via administration of a composition according to the present disclosure.

The term "treatment" as used herein means all actions that alleviate or beneficially change symptoms due to cancer or the like via administration of a concentration according to the present disclosure.

The term "individual" as used herein refers to a subject to which the composition of the present disclosure may be administered, but the subject is not limited.

In the present specification, the pharmaceutical composition may be in the form of capsules, tablets, granules, an injection, an ointment, powder, or a beverage, and the pharmaceutical composition may be used for humans. The pharmaceutical composition is not limited to the above examples, and may be formulated in the form of oral preparations such as powder, granules, capsules, tablets, an aqueous suspension, and the like, preparations for external application, suppositories, and sterile injection solutions, according to general methods. The pharmaceutical composition of the present disclosure may include a pharmaceutically acceptable carrier. The pharmaceutically acceptable carrier may be a binder, a lubricant, a disintegrant, an excipient, a solubilizing agent, a dispersant, a stabilizer, a suspension agent, a pigment, a flavoring, or the like in the case of oral administration, may be used in combination with a buffer, a preservative, an analgesic agent, a solubilizer, an isotonic agent, a stabilizer, or the like in the case of injections, and may be a base, an excipient, a lubricant, a preservative, or the like in the case of topical administration. Preparations of the pharmaceutical composition of the present disclosure may be formulated in a variety of ways by mixing with the above-described pharmaceutically acceptable carrier(s). For example, preparations for oral administration may be formulated in the form of tablets, troches, capsules, elixirs, suspensions, syrups, wafers, or the like, and preparations for injections may be formulated in unit dosage ampoules or in multiple dosage form. In addition, preparations of the pharmaceutical composition may be formulated in the form of solutions, suspensions, tablets, capsules, sustained release type preparations, or the like.

Meanwhile, examples of suitable carriers, excipients and diluents for formulation include lactose, dextrose, sucrose, sorbitol, mannitol, xylitol, erythritol, maltitol, starch, acacia gum, alginates, gelatin, calcium phosphate, calcium silicate, cellulose, methyl cellulose, micro-crystalline cellulose, polyvinylpyrrolidone, water, methylhydroxy benzoate, propylhydroxy benzoate, talc, magnesium stearate, mineral oil, and the like. In addition, the pharmaceutical composition may further include a filler, an anti-coagulant, a lubricant, a wetting agent, a flavoring, an emulsifier, a preservative, or the like.

Administration routes of the pharmaceutical composition according to the present disclosure include, but are not limited to, oral administration, intravenous administration, intramuscular administration, intraarterial administration, intramedullary administration, intradural administration, intracardiac administration, transdermal administration, subcutaneous administration, intraperitoneal administration, intranasal administration, intestinal administration, topical administration, sublingual administration, and rectal administration. The pharmaceutical composition may be administered orally or parenterally. The term "parenteral" as used herein is intended to include subcutaneous, intradermal, intravenous, intramuscular, intraarticular, intrabursal, intrasternal, intradural, intralesional, and intracranial injections or injection techniques. The pharmaceutical composition of the present disclosure may also be administered in the form of a suppository for rectal administration.

The pharmaceutical composition of the present disclosure may vary depending on various factors including the activity of the used specific compound, age, body weight, general health, gender, diet, administration time, administration route, drug combination, and the severity of a particular disease to be prevented or treated, and a dosage of the pharmaceutical composition varies according to the condition and body weight of a patient, the severity of disease, drug form, administration route, and administration period, but may be appropriately selected by one of ordinary skill, and may range from about 0.0001 mg/kg/day to about 50 mg/kg/day or about 0.001 mg/kg/day to about 50 mg/kg/day. The pharmaceutical composition may be administered once or multiple times a day. The dosage is not intended to limit the scope of the present disclosure in any way. The pharmaceutical composition according to the present disclosure may be formulated into pills, sugar-coated tablets, capsules, a liquid, a gel, a syrup, a slurry, or a suspension.

Hereinafter, examples will be described to aid in understanding of the present disclosure. However, the following examples are provided only to facilitate the understanding of the present disclosure and are not intended to limit the scope of the present disclosure.

EXAMPLES

Example 1

Preparation of Iron/Hyaluronic Acid Nanoparticles 5 mg of sodium hyaluronate was added to 50 mL of deionized water (DI) and stirred until hyaluronic acid was completely dissolved. 10 mL of deionized water to which 99.4 mg of $FeCl_2 \cdot 4H_2O$ was added to the solution in which hyaluronic acid was dissolved at a rate of 1 mL/min and stirred for 30 minutes, and then 10 mL of deionized water to which 149.1 mg of $FeCl_2 \cdot 6H_2O$ was added was added thereto at a rate of 1 mL/min and stirred for 1 hour. After adjusting the pH of the solution to 10 by adding 1.5 M ammonia water and stirring the solution for 30 minutes, a product was separated from the solution using a strong neodymium magnet. The separated product was washed several times with deionized water, and then impurities were cleanly removed by using a water sonicator and redispersed in 50 mL of 0.005 M HCl. The dispersed nanoparticles were purified by dialysis (MWCO 3.5K) for 24 hours to prepare Fe/hyaluronic acid nanoparticles (FHA NPs). The prepared FHA NPs were stored at −4° C.

Figure 1B:
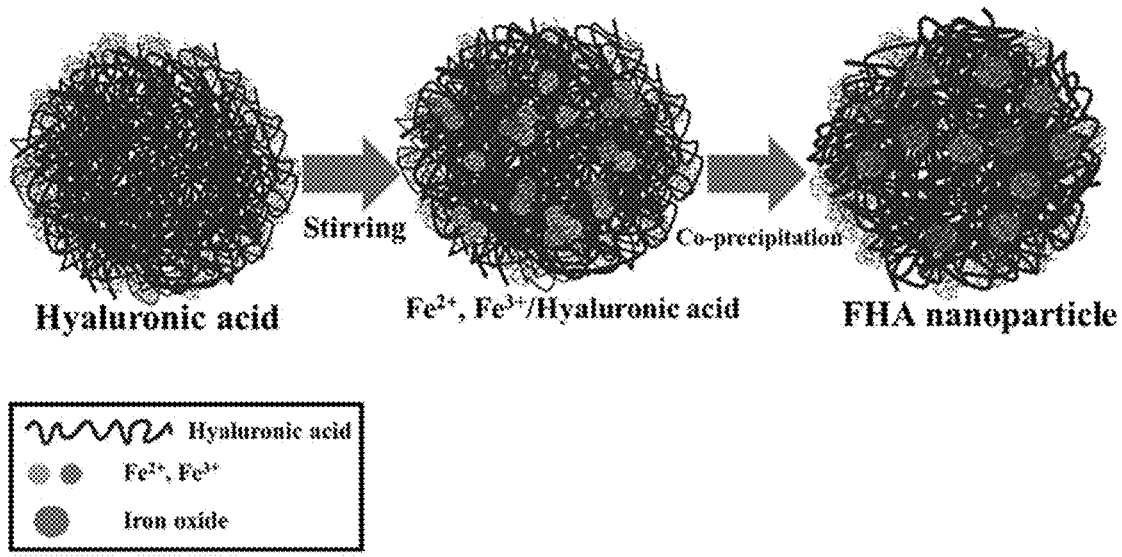
FIG. 1B is a schematic view illustrating a preparation method of iron/hyaluronic acid nanoparticles according to the present disclosure.

A cancer cell killing mechanism of the FHA NPs is illustrated in FIG. 1A, and a method of preparing the nanoparticles is schematically illustrated in FIG. 1B. As illustrated in FIG. 1B, the FHA NPs according to the present disclosure are prepared such that, when mixing hyaluronic acid nanoparticles with a divalent Fe ion and a trivalent Fe ion to allow a reaction to occur therebetween, an Fe cation and a carboxyl group ($COO^-$) of hyaluronic acid are bound and aggregated, thereby forming a nano-sized conjugate.

Example 2

Analysis of FHA NPs 2.1. Size Analysis of FHA NPs

The size of the FHA NPs prepared in the same manner as in Example 1 was measured using dynamic light scattering (DLS). More specifically, the concentration of hyaluronic acid (HA) was adjusted to 0.005 wt %, 0.01 wt %, 0.05 wt %, or 0.5 wt % and FHA NPs were prepared using each concentration of HA, and the size of the prepared nanoparticles was measured using Zetasizer Nano ZS 3600 (Malvern Instruments). The results thereof are shown in FIG. 2A.

Figure 2A:
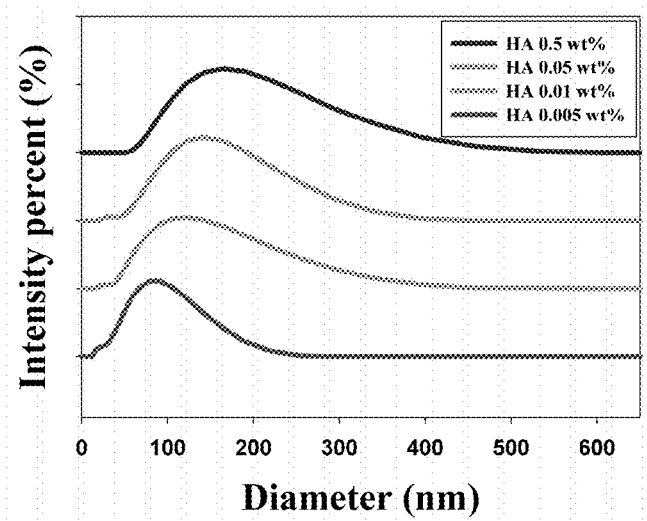
FIG. 2A illustrates the results of measuring the size of iron/hyaluronic acid nanoparticles according to an embodiment of the present disclosure.

As shown in FIG. 2A, it was confirmed that the size of the nanoparticles prepared according to the concentration of HA was adjusted, and 0.01 wt % of HA was selected to prepare nanoparticles having an average diameter of 105.7 mm and a standard deviation of 13.3 nm, and then a subsequent experiment was conducted. The FHA NPs according to the present disclosure had an average diameter of 100 nm, and not only exhibited active targeting for CD44, but also exhibited a passive targeting effect through enhanced permeability and retention (EPR), from which it was confirmed that the FHA NPs were able to significantly enhance cancer cell-specific delivery capability.

2.2. Absorption Spectrum Analysis of FHA NPs

To analyze the electronic structural properties of the FHA NPs, an UV-visible absorption spectrum was measured using a microplate reader (Synergy H1, Hybrid reader, Bio Tek). More specifically, FHA NPs prepared in the same manner as in Example 1 were diluted to a concentration of 6.25 µg/mL, 12.5 µg/mL, 25 µg/mL, 50 µg/mL, 100 µg/mL, or 200 µg/mL and the absorption spectrum of each case was measured, and absorption spectra of HA, $FeCl_2$, and $FeCl_3$, which were used in the preparation of nanoparticles, as controls, were also measured. The results thereof are illustrated in FIG. 2B.

Figure 2B:
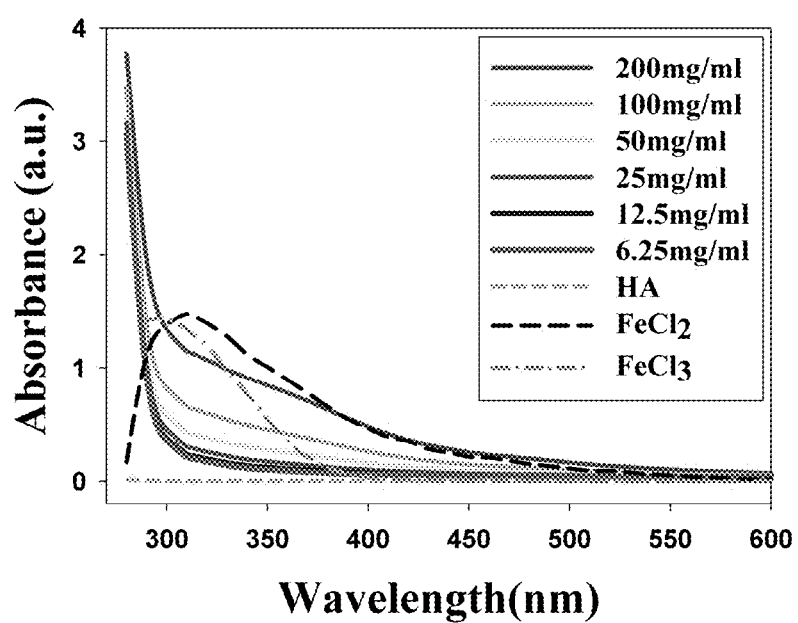
FIG. 2B illustrates the absorption spectrum analysis results of iron/hyaluronic acid nanoparticles according to an embodiment of the present disclosure.

As shown in FIG. 2B, it was confirmed that the absorption value at each wavelength changes as the concentration of nanoparticles is increased. It was also confirmed that the absorption spectrum of the FHA NPs was different from the absorption spectrum of $FeCl_2$ or $FeCl_3$ used as the raw material.

2.3. Morphology and Surface Analysis of FHA NPs

The morphology of the FHA NPs was observed using an energy-filtering transmission electron microscope (TEM, LIBRA 120, Carl Zeiss) operating at an acceleration voltage of 120 kV, and the surfaces of the nanoparticles were observed using a field emission scanning electron microscope (FE-SEM, JSM-7800F Prime, JEOL Ltd.). More specifically, 5 µL of 0.1 wt % nanoparticles prepared in the same manner as in Example 1 was placed on silver foil, dried in a vacuum chamber, and coated with platinum for observation using a SEM, and for TEM observation, 5 µL of 0.1 wt % nanoparticles was placed on a TEM grid made of mesh copper, and then dried in a vacuum chamber and observed. Images acquired using a SEM and a TEM are shown in FIG. 2C.

Figure 2C:
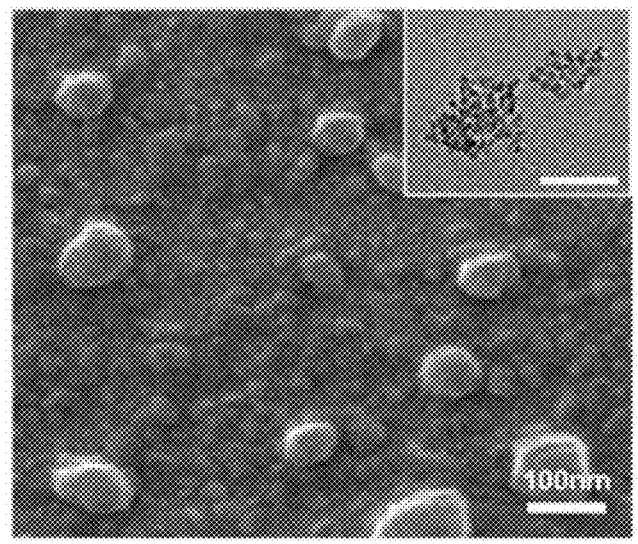
FIG. 2C illustrates the results of observing iron/hyaluronic acid nanoparticles according to an embodiment of the present disclosure under a scanning electron microscope and a transmission electron microscope.

As shown in FIG. 2C, it was confirmed that spherical nanoparticles having an average diameter of 100 nm were normally prepared.

In addition, the samples observed with a TEM were subjected to Energy Dispersive Spectrometry (EDS) to identify components included in the FHA NPs. The results thereof are shown in FIG. 2D.

Figure 2D:
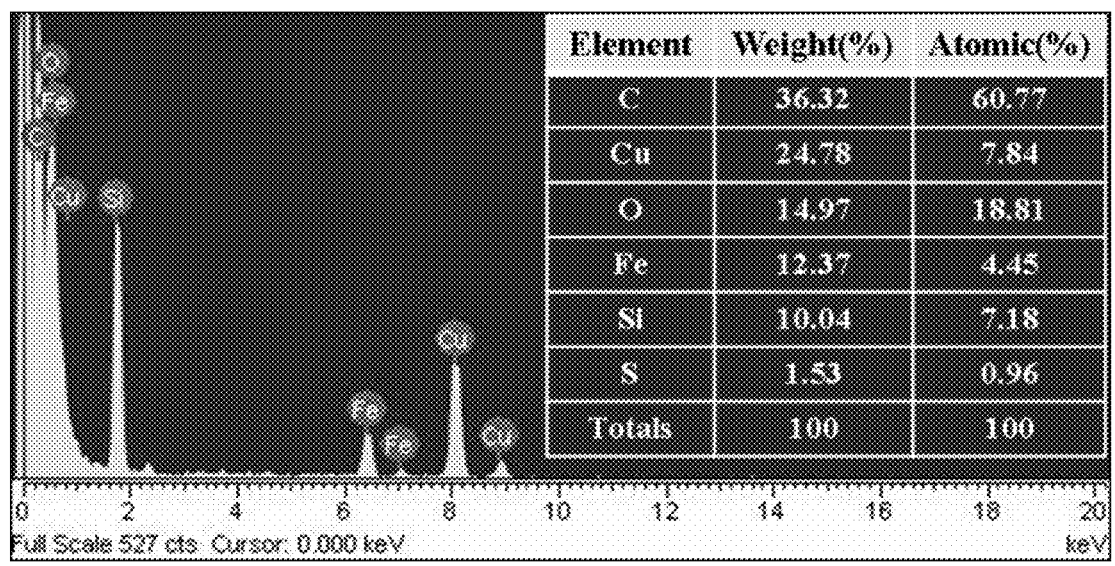
FIG. 2D illustrates the results of confirming components included in iron/hyaluronic acid nanoparticles according to an embodiment of the present disclosure by energy dispersive spectroscopy.

As illustrated in FIG. 2D, iron components were observed in addition to TEM grid components. From the above results, it was confirmed that iron was bonded in the FHA NPs.

2.4. Iron Particle Analysis of FHA NPs

To confirm the state of bound iron particles in the FHA NPs, the FHA NPs were analyzed by X-ray diffraction (XRD) analysis using an X-ray diffractometer (Rigaku, SmartLab). Hyaluronic acid was used as a control. The results thereof are shown in FIG. 2E.

Figure 2E:
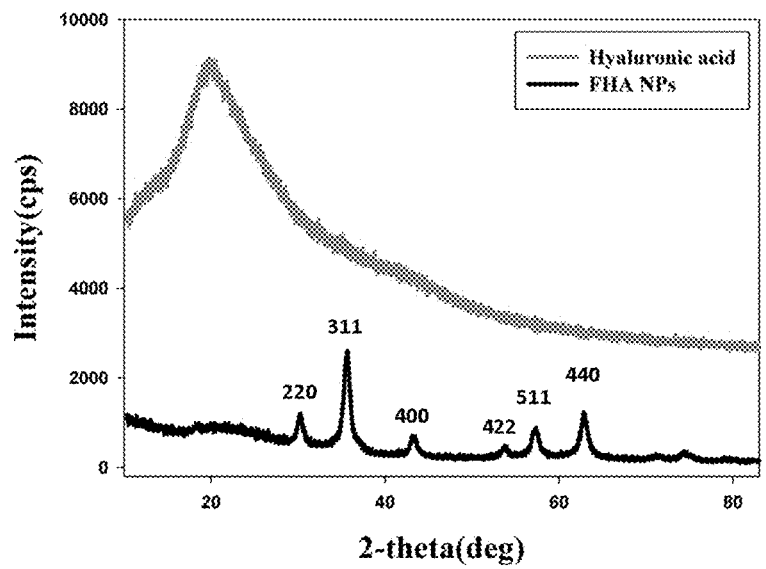
FIG. 2E illustrates the results of confirming bound iron particles in iron/hyaluronic acid nanoparticles according to an embodiment of the present disclosure by X-ray diffraction analysis.

As illustrated in FIG. 2E, it was confirmed that the intensity shown at nanoparticle 2-theta values of 30.3°, 35.8°, 43.5°, 53.9°, 57.3°, and 62.8° was consistent with $Fe_3O_4$. From the above result, it was confirmed that iron bound in the FHA NPs was $Fe_3O_4$.

In addition, the amount of iron particles bound in the FHA NPs was measured using an inductively coupled plasma-atomic emission spectroscope (ICP-AES, Optima 8300, Perkin-Elmer). The results thereof are shown in FIG. 2F.

Figure 2F:
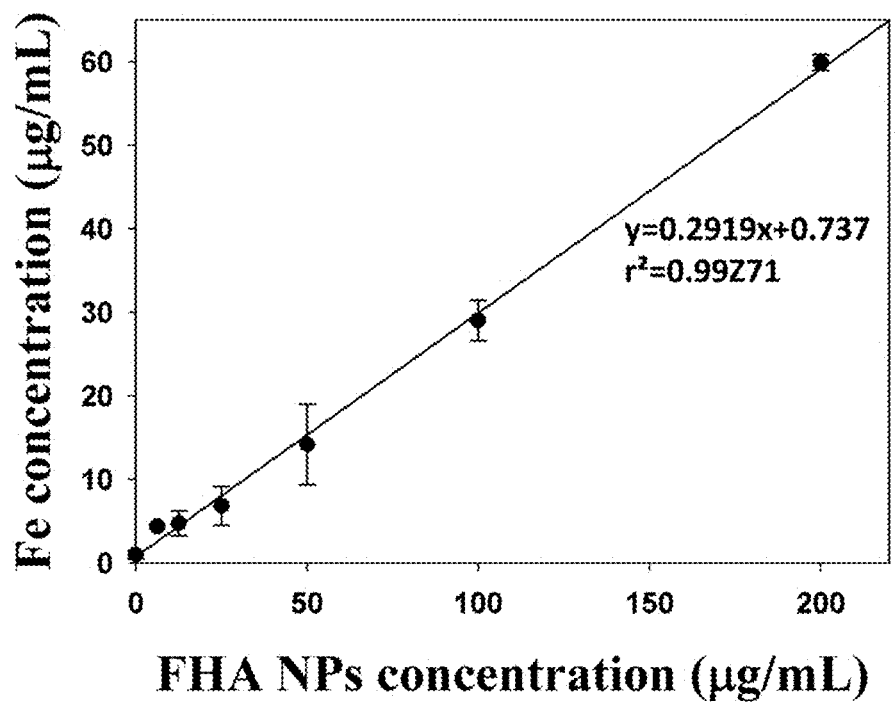
FIG. 2F illustrates the results of confirming the amount of bound iron particles in iron/hyaluronic acid nanoparticles according to an embodiment of the present disclosure by inductively coupled plasma atomic emission spectroscopy.

As illustrated in FIG. 2F, it was confirmed that the amount of iron bound in the nanoparticles increased in proportion to the concentration of the FHA NPs, and a significant linear result of 'y=0.2919x+0.737' was shown. From the above results, it was confirmed that $Fe_3O_4$ was bound, at a uniform concentration, to hyaluronic acid particles of the FHA NPs prepared using the method of Example 1.

2.5. Surface Charge Measurement of FHA NPs

The surface charge of the FHA NPs was confirmed by measuring zeta potential. More specifically, 8 mg/mL of the FHA NPs were diluted 50-fold in 1 mL of a 0.005 M HCl solution with pH of 4, 1 mL of phosphate buffered saline (PBS) with pH of 7, or 1 mL of 0.005 M NaOH with pH of 10 to prepare samples, and the zeta potential of each sample was measured using the Zetasizer Nano ZS (Malvern Instruments), and an average value was calculated after three repeated measurements for each sample. The results thereof are shown in FIG. 2G.

Figure 2G:
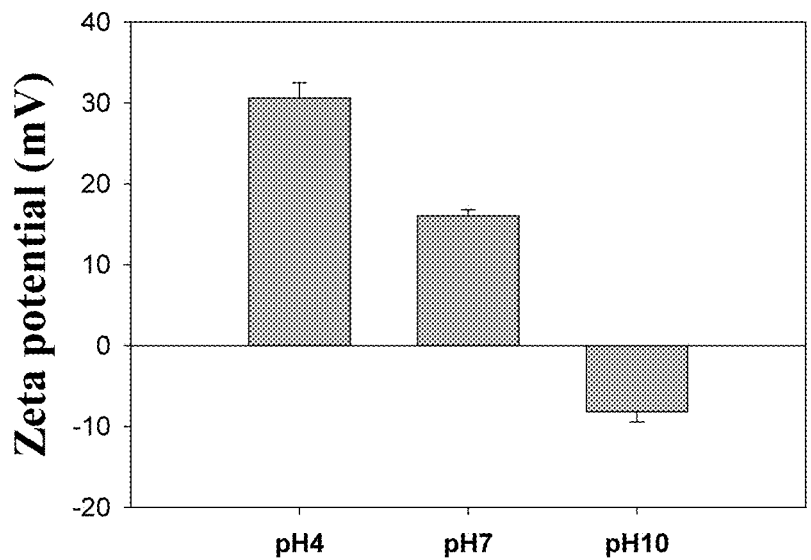
FIG. 2G illustrates the results of confirming the surface charge of iron/hyaluronic acid nanoparticles according to an embodiment of the present disclosure by zeta potential.

As illustrated in FIG. 2G, it was confirmed that a zeta potential of 30.59 mV and a standard deviation of 1.92 mV were shown at pH 4, a zeta potential of 16.1 mV and a standard deviation of 0.77 mV were shown at pH 7, and a zeta potential of −8.17 mV and a standard deviation of 1.29 mV were shown at pH 10. The zeta potential value is changed by binding due to the interaction between materials included in a nanostructure, and when the zeta potential is low, phenomena such as Ostwald ripening are prevented due to an increase in increased repulsion of particles so that stable nanoparticles that do not aggregate can be maintained. Thus, it was confirmed that the FHA NPs according to the present disclosure having a zeta potential of 30 mV were able to be stably present in a homogeneous state.

2.6. Stability Confirmation of FHA NPs

To primarily confirm the pH stability of the FHA NPs, the FHA NPs were diluted 50-fold in 3 mL of a 0.005 M HCl solution with pH of 4, 3 mL of PBS with pH of 7, or 3 mL of 0.005 M NaOH with pH of 10 to prepare samples, and the size of the nanoparticles was measured using the same method as that used in Example 2.1. The results thereof are shown in FIG. 2H.

Figure 2H:
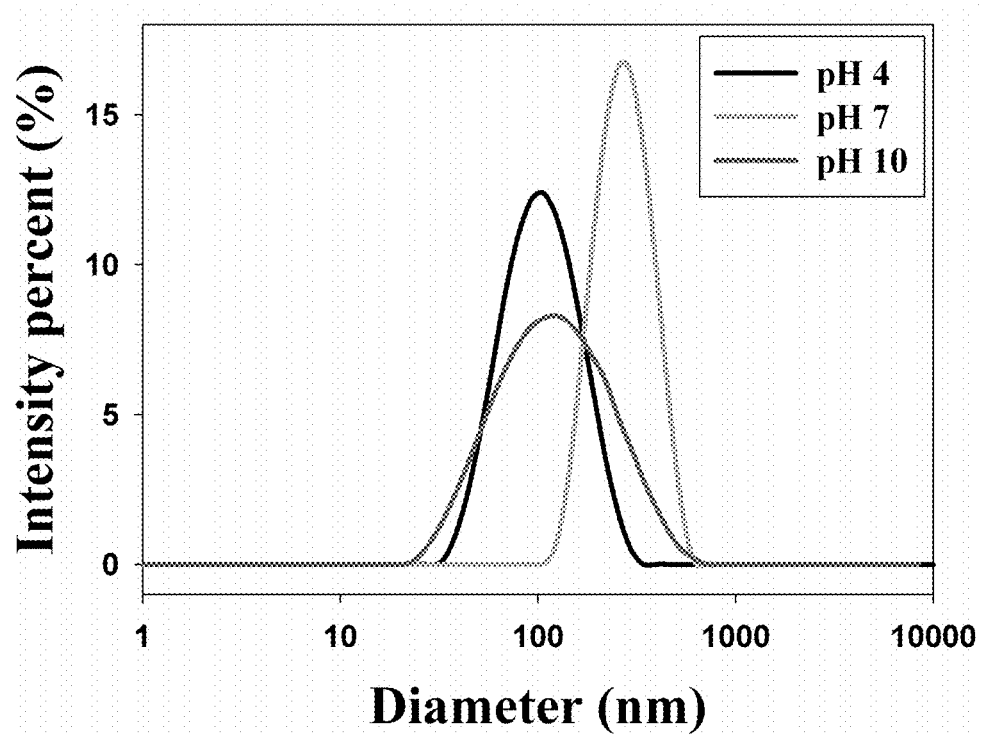
FIG. 2H illustrates the results of confirming the pH stability of iron/hyaluronic acid nanoparticles according to an embodiment of the present disclosure by the size of nanoparticles.

As shown in FIG. 2H, the average diameter of the nanoparticles at pH 4 was maintained at 100 nm, whereas the diameter of the particles at pH 7 was significantly increased. In addition, the average particle of the nanoparticles at pH 10 was 150 nm, but the size distribution increased, from which it was confirmed that the stability of the nanoparticles was reduced. From the above results, it was confirmed that the FHA NPs could be stably stored in a 0.005 M HCl solution at pH 4.

To confirm whether the stability of the FHA NPs is maintained even during long-term storage, the nanoparticles added to a 0.005 M HCl solution with pH of 4 were stored for 180 days, and the diameter and polydispersity of the nanoparticles were investigated. The polydispersity was identified using a polydispersity index (PDI). The results thereof are shown in FIG. 2I.

Figure 2I:
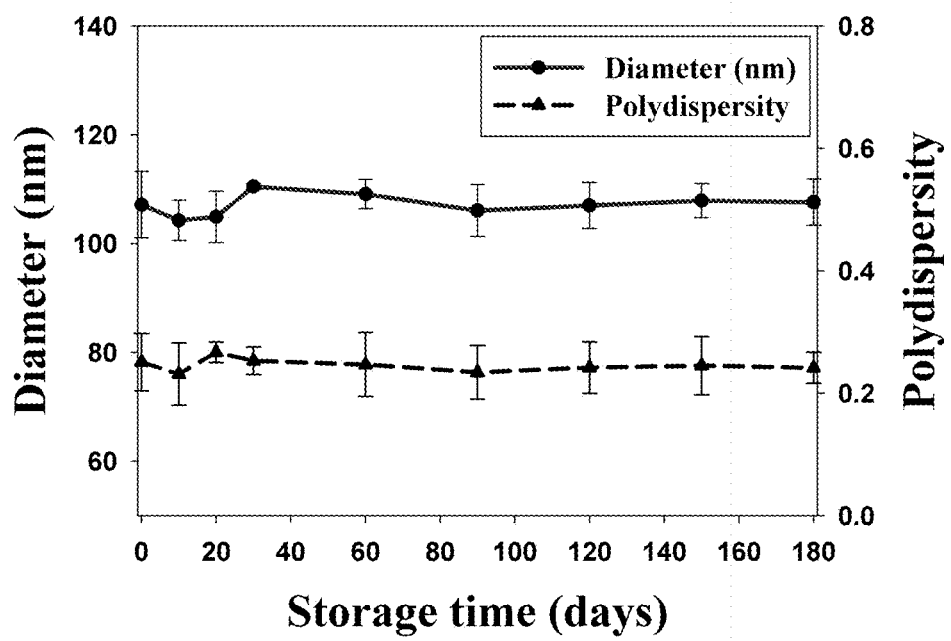
FIG. 2I illustrates the results of confirming the stability of iron/hyaluronic acid nanoparticles according to an embodiment of the present disclosure by the size of nanoparticles and polydispersity.

As illustrated in FIG. 2I, it was confirmed that there was no significant change in the diameter and polydispersity of the FHA NPs for 180 days. From the above result, it was confirmed that the stability of the FHA NPs according to the present disclosure was maintained even during long-term storage.

From the above results, it was confirmed that, in the FHA NPs prepared using the method of Example 1, iron particles of $Fe_3O_4$ were uniformly bound to hyaluronic acid nanoparticles having an average diameter of 100 nm, and the FHA NPs exhibited excellent stability.

Example 3

Confirmation of Anticancer Effect of FHA NPs 3.1. Confirmation of Anticancer Effect through CCK-8 Assay To confirm the anticancer effect of the FHA NPs prepared using the same method as that used in Example 1, various kinds of cell lines were treated with the nanoparticles and cell viability was measured through CCK-8 assay. For use in experiments, human fibroblast cells (HFB), human breast adenocarcinoma cells (MCF7), human colon carcinoma cells (HCT116), human lung carcinoma cells (A549), and human ovarian cancer cells were purchased from the Korean Cell Line Bank, and the human fibroblasts were cultured in Dulbecco's Modified Eagle Medium (DMEM) supplemented with 10% fetal bovine serum (FBS) and 1% penicillin/streptomycin, and the cancer cell lines were cultured in RPMI 1640 supplemented with 10% FBS and 1% penicillin/streptomycin. To confirm cytotoxicity, the cell lines were added onto a 96-well plate at a density of $1\times10^4$ cells per well and cultured for 24 hours. Then, the cultured cells were washed once with Dulbecco's PBS (DPBS) and treated with 6.25 μg/mL, 12.5 μg/mL, 25 μg/mL, 50 μg/mL, 100 μg/mL, or 200 μg/mL of an FHA NP suspension diluted with a serum-free medium, and after incubation at 37° C. for 1 hour, 3 hours, 6 hours, or 12 hours, 10 mL of a CCK-8 solution included in a cell counting kit-8 (CCK-8, EZ-Cytox, DoGen) was added to each well, followed by further incubation for 3 hours. Then, optical density (OD) at 450 nm of each well was measured using a microplate reader (Synergy H1, Hybrid reader, Bio Tek). Cell viability was calculated by substituting the measured OD values into the following equation. In the following equation, experiment denotes cells treated with the FHA NPs, and control denotes cells that were not treated with the FHA NPs. The results thereof are shown in FIGS. 3A to 3D.

$$\text{Cell viability}(\%) = \frac{OD(\text{experiment}) - OD(\text{blank})}{OD(\text{control}) - OD(\text{blank})} \times 100$$

Figure 3A:
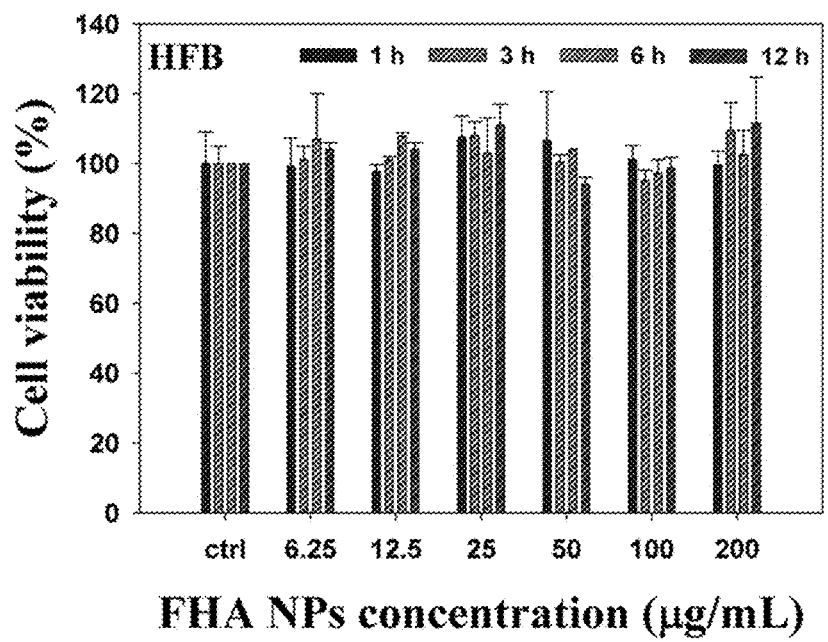
FIG. 3A illustrates the results of confirming the anticancer effect of iron/hyaluronic acid nanoparticles according to an embodiment of the present disclosure in human fibroblasts.
Figure 3B:
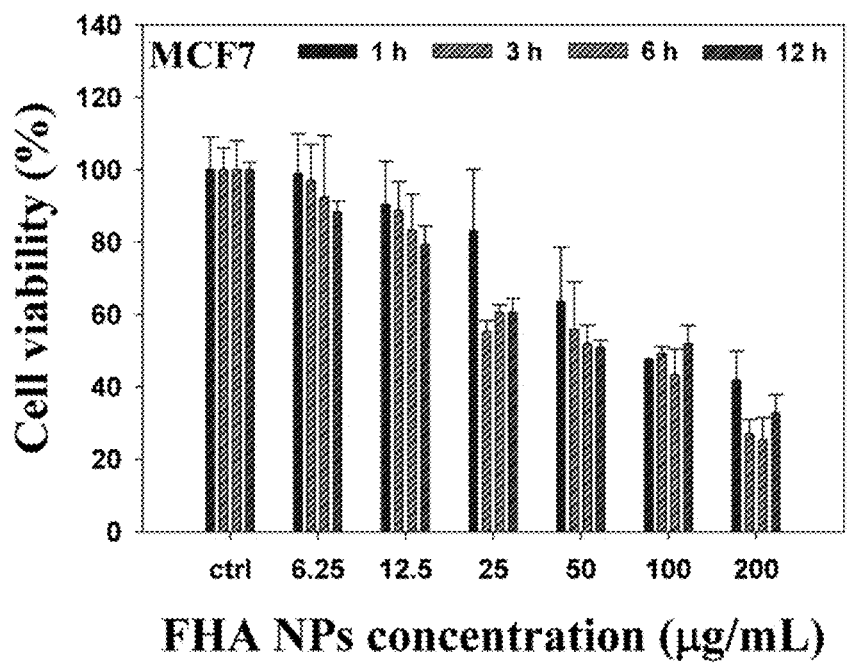
FIG. 3B illustrates the results of confirming the anticancer effect of iron/hyaluronic acid nanoparticles according to an embodiment of the present disclosure in a human breast cancer cell line.
Figure 3C:
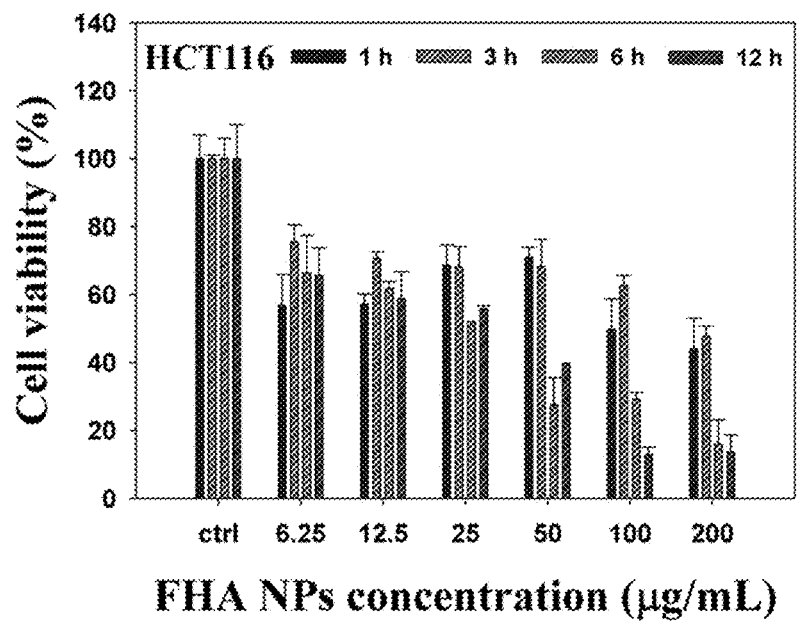
FIG. 3C illustrates the results of confirming the anticancer effect of iron/hyaluronic acid nanoparticles according to an embodiment of the present disclosure in a human colon cancer cell line.
Figure 3D:
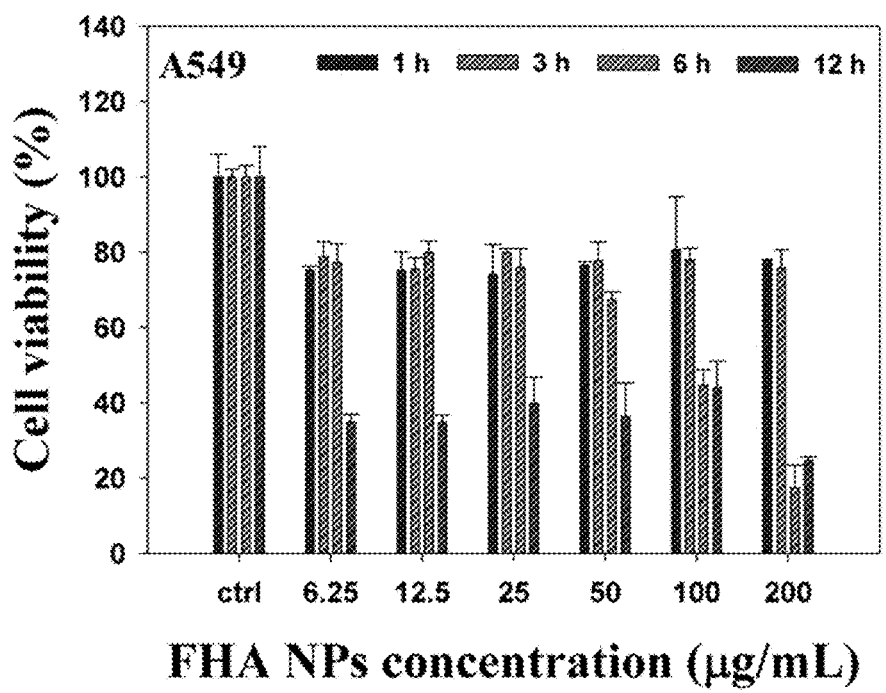
FIG. 3D illustrates the results of confirming the anticancer effect of iron/hyaluronic acid nanoparticles according to an embodiment of the present disclosure in a human lung cancer cell line.
Figure 3E:
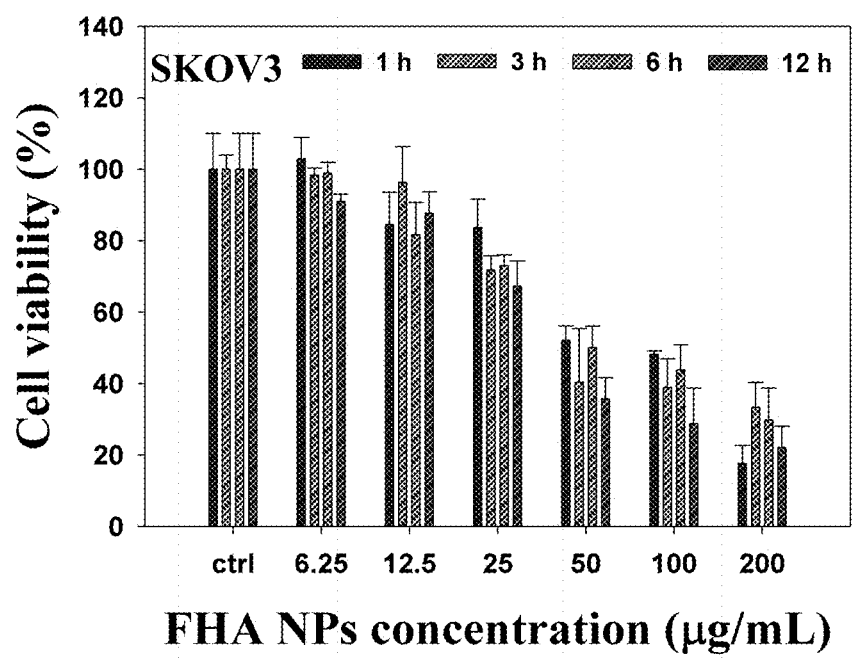
FIG. 3E illustrates the results of confirming the anticancer effect of iron/hyaluronic acid nanoparticles according to an embodiment of the present disclosure in a human ovarian cancer cell line.

As illustrated in FIG. 3A, it was confirmed that cell death was not induced in human fibroblasts, which are a normal cell line, even by treatment with a high concentration of 200 μg/mL of the FHA NPs. In contrast, as illustrated in FIGS. 3B to 3E, it was confirmed that, the greater the concentration of the FHA NPs in cancer cells and the longer the treatment time, the greater the cell death.

3.2. Confirmation of Anticancer Effect Using Live/Dead Viability/Cytotoxicity Kit To reconfirm the anticancer effect of the FHA NPs prepared using the same method as that used in Example 1, the degree of cell death was examined using a Live/Dead viability/cytotoxicity kit (Invitrogen). More specifically, the cells treated with the FHA NPs in the same manner as in Example 3.1 were cultured for 12 hours, and then washed three times with a phosphate buffer solution. Then, the cells were treated with 2 mM Calcein AM and 4 μM ethidium homodimer-1 (ethyl-D) and a reaction was allowed to occur therebetween for 30 minutes. Thereafter, the cells were observed using a laser scanning microscope (Carl Zeiss). The results thereof are shown in FIG. 4.

Figure 4:
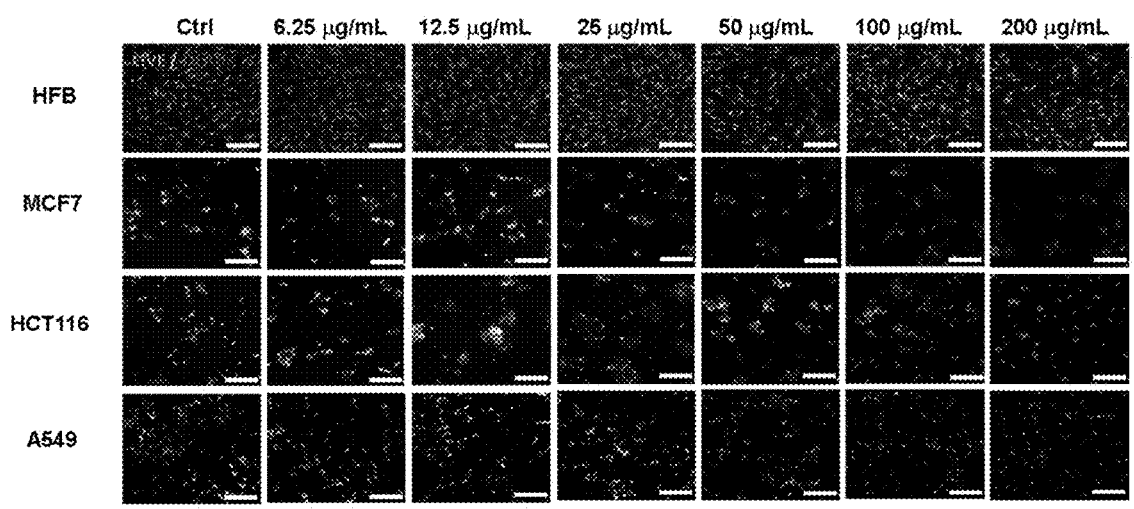
FIG. 4 illustrates the results of confirming the anticancer effect of iron/hyaluronic acid nanoparticles according to an embodiment of the present disclosure using a live/dead viability/cytotoxicity kit, wherein scale bars indicate 100 μm.

As shown in FIG. 4, through no red fluorescence being observed, it was confirmed that cell death was not induced in the fibroblasts, which are a normal cell line. In contrast, it was confirmed that, as the concentration of the treated FHA NPs increased, red fluorescence significantly increased in cancer cells.

From the above results, it was confirmed that the FHA NPs according to the present disclosure did not exhibit cytotoxicity in normal cells, while exhibiting a selective anticancer effect in cancer cells.

Example 4

Identification of Effect of FHA NPs on Secretion of Reactive Oxygen Species

To confirm the effect of the FHA NPs on the secretion of reactive oxygen species in cancer cells, cells treated with the FHA NPs in the same manner as in Example 3.1 were cultured for 12 hours, and then washed three times with a phosphate buffer solution. Subsequently, the cells were treated with 300 μL of a CellROX orange oxidative stress reagent (Invitrogen) and incubated at 37° C. for 30 minutes, and then treated with 4',6-diamidino-2-phenylindole (DAPI, Sigma Aldrich) and further incubated for 5 minutes. Then, fluorescence was observed using a laser scanning microscope (Carl Zeiss), and red fluorescence images acquired through the microscope were quantified using FCS Express V3 software (De Novo Software). The results thereof are shown in FIGS. 5A and 5B.

Figure 5A:
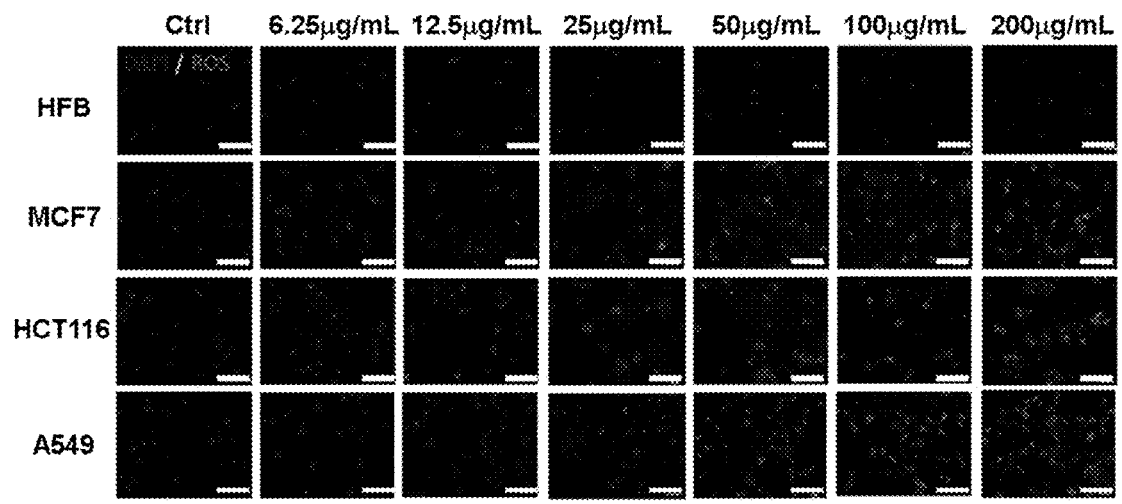
FIG. 5A illustrates the effect of iron/hyaluronic acid nanoparticles according to an embodiment of the present disclosure on the secretion of reactive oxygen species using a microscope.
Figure 5B:
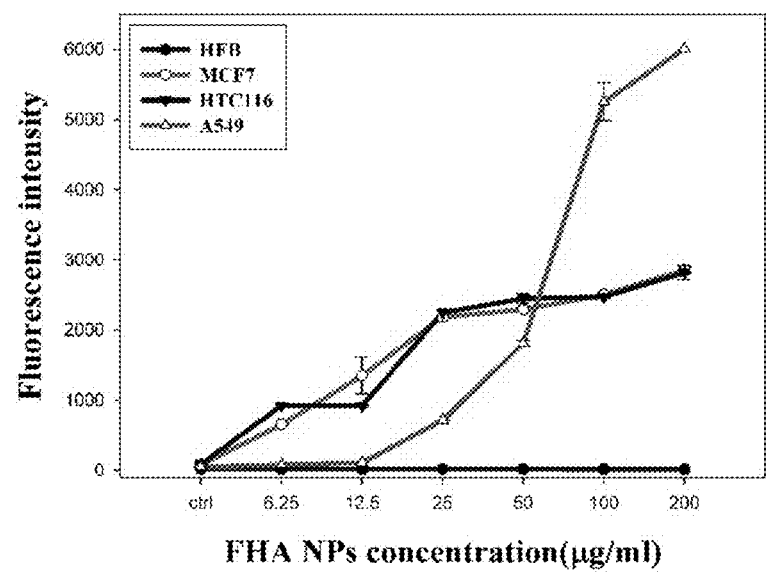
FIG. 5B illustrates the results of quantifying fluorescence values of images acquired using the microscope.

As illustrated in FIG. 5A, it was confirmed that, while only the nuclei of blue fluorescence stained with DAPI were observed in fibroblasts, which are a normal cell line, red fluorescence, which indicates reactive oxygen species, was observed in the vicinity of the nuclei in cancer cell lines. It was also confirmed as illustrated in FIG. 5B that, as the concentration of the treated FHA NPs increased, red fluorescence values which indicate reactive oxygen species significantly increased. From the above results, it was confirmed that the FHA NPs increased the content of intracellular reactive oxygen species in cancer cells specifically.

Example 5

Confirmation of Cell Death Mechanism of FHA NPs 5.1. Confirmation of Cell Death Mechanism Using Real Time-Polymerase Chain Reaction (RT-PCR)

RT-PCR was performed to confirm the cell death mechanism of the FHA NPs. More specifically, cells treated with 200 μg/mL of the FHA NPs in the same manner as in Example 3.1 were cultured for 12 hours, and then washed three times using a phosphate buffer solution. Subsequently, total RNA was isolated from the cells using TRIzol, and cDNA was synthesized using a cDNA synthesis kit (Maxime RT PreMix, Intron) using the isolated RNA as a template. Then, RT-PCR was performed in QuantStudio5 Real-Time PCR System (Applied Biosystems) using RealMOD Green SF 2X qPCR Mix (Intron). RT-PCR was performed at 95° C. for 10 minutes, and then the cycle of 95° C. for 15 seconds, 60° C. for 30 seconds, and 72° C. for 5 minutes was repeated 40 times, and the sequences of primers used in RT-PCR are shown in Table 1 below. The expression of the BCL2 associated X (BAX) gene was confirmed as a marker of apoptosis, the expression of the receptor-interacting serine/threonine-protein kinase 1 (RIPK1) gene was identified as a marker of necrosis, and the expression of the glutathione peroxidase 4 (GPX4) gene, which is a negative gene, was confirmed as a marker of ferroptosis. Each mRNA expression amount was quantified by the ΔΔCT method compared to the expression level of β-actin as a control, and the results thereof are shown in FIG. 6.

TABLE 1

| Gene | Primer sequence (5' → 3') | SEQ ID NO: |
|---|---|---|
| Bax | Forward Primer: AGGCGGCGGGCCCACCAGCTC | 1 |
|  | Reverse Primer: CATCAGCAAACATGTCAGCTG | 2 |
| Ripk1 | Forward Primer: GGCATTGAAGAAAAATTTAGGC | 3 |
|  | Reverse Primer: TCACAACTGCATTTTCGTTTG | 4 |
| GPX4 | Forward Primer: ACAAGAACGGCTGCGTGGTGAA | 5 |
|  | Reverse Primer: GCCACACACTTGTGGAGCTAGA | 6 |
| β-actin | Forward Primer: GTGGGCCGCTCTAGGCACCAA | 7 |
|  | Reverse Primer: CTT-TAGCACGCACTGTAGTTTCTC | 8 |

Figure 6:
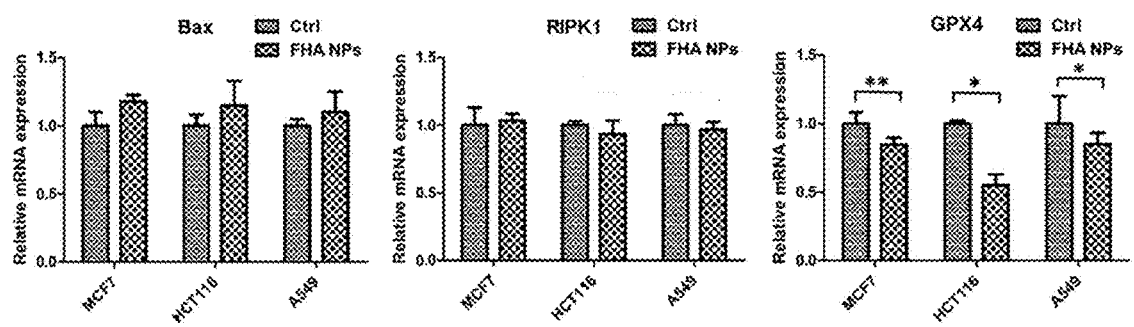
FIG. 6 illustrates the results of confirming the cell death mechanism of iron/hyaluronic acid nanoparticles according to an embodiment of the present disclosure by real time-polymerase chain reaction (RT-PCR), wherein * denotes $P<0.05$,  denotes $P<0.01$, * denotes $P<0.001$.

As illustrated in FIG. 6, it was confirmed that the apoptosis- or necrosis-related gene did not exhibit a significant difference in expression, but in the case of the GPX4 gene, which is a ferroptosis-related gene, gene expression was significantly reduced in cells treated with the FHA NPs. From the above results, it was confirmed that the FHA NPs according to the present disclosure induced the death of cancer cells through ferroptosis.

5.2. Confirmation of Cell Death Mechanism Using Inhibition Assay

To reconfirm whether the FHA NPs have a cancer cell killing effect through ferroptosis, inhibition assay was performed. It is known that α-tocopherol, which is known as vitamin E, and Ferrostatin-1 inhibit lipid peroxidation and thus inhibit cell death, while RSL3 inactivates GPX4 to increase the expression of reactive oxygen species, thereby promoting lipid peroxidation to induce cell death. First, to confirm the effective concentration of each compound, cell viability was measured in the same manner as in Example 3.1. More specifically, cells were treated with 200 μg/mL of the FHA NPs and each compound according to various concentrations and incubated for 12 hours, and then cell viability was measured using CCK-8. The results thereof are shown in FIG. 7A.

Figure 7A:
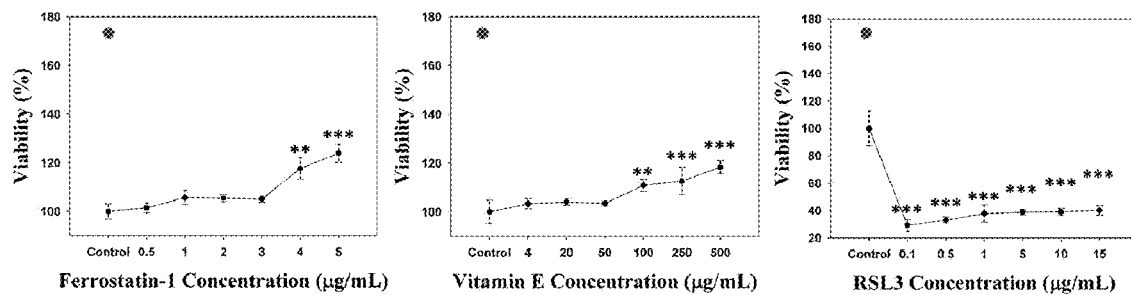
FIG. 7A illustrates the results of confirming the optimal concentrations of compounds for inhibition assay according to an embodiment of the present disclosure, wherein * denotes $P<0.05$,  denotes $P<0.01$, * denotes $P<0.001$.

As illustrated in FIG. 7A, it was confirmed that ferrostatin-1 and vitamin E increased cell viability, whereas RSL3 reduced cell viability. The red dot at the left top of each graph denotes the viability of a control that was not treated with the FHA NPs. Through the above results, a subsequent experiment was carried out using ferrostatin-1 at a concentration of 4 μg/mL, vitamin E at a concentration of 100 μg/mL, and RSL3 at a concentration of 1 μg/mL.

Each cell line was treated with a combination of 200 μg/mL of the FHA NPs and each compound and incubated for 12 hours, and then cell viability was measured using CCK-8. Assuming that the viability of an experimental group treated with the FHA NPs alone is 100%, the viabilities of the other experimental groups were calculated. The results thereof are shown in FIG. 7B.

Figure 7B:
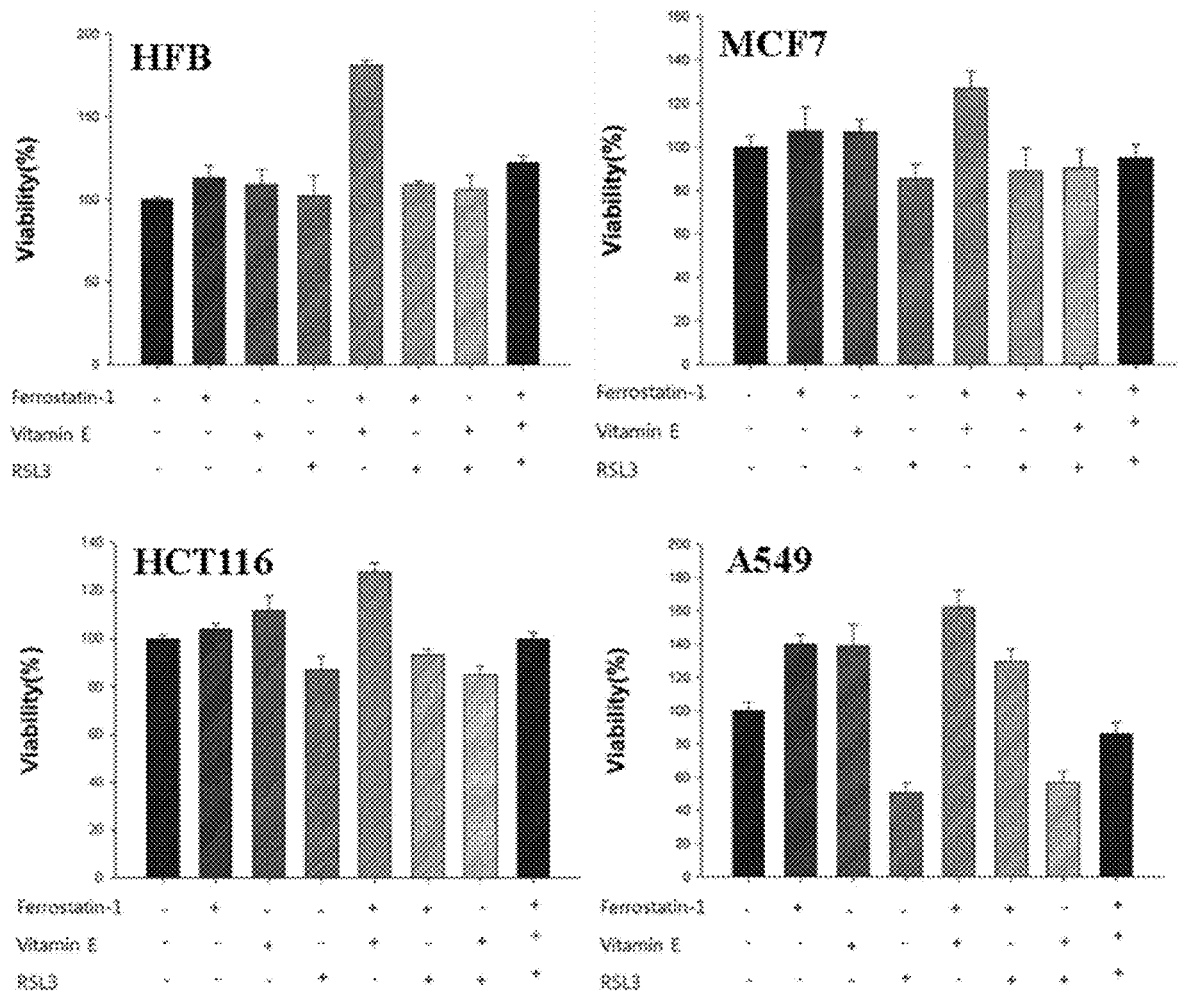
FIG. 7B illustrates the results of confirming the cell death mechanism of iron/hyaluronic acid nanoparticles according to an embodiment of the present disclosure by inhibition assay.

As illustrated in FIG. 7B, it was confirmed that, in cancer cell lines, cell viability was reduced in an experimental group treated with RSL3 alone, whereas cell viability was increased in an experimental group treated with both ferrostatin-1 and vitamin E. It was also confirmed that cell viability was significantly changed through an increase or decrease of the drugs.

From the above results, it was confirmed that the FHA NPs according to the present disclosure induced selective cancer cell death through ferroptosis.

Example 6

Confirmation of Iron Particle Migration of FHA NPs

To confirm whether iron particles of the FHA NPs migrate into cells, Prussian blue staining was performed. Prussian blue chelates iron ions when iron is contained in cells, thus showing a blue color. For Prussian blue staining, cells were treated with the FHA NPs in the same manner as in Example 3.1 and incubated for 12 hours. The cells were fixed by treatment with 4% paraformaldehyde and a reaction therebetween for 15 minutes, and the fixed cells were treated with 5 wt % Prussian blue ($C_6Fe_2KN_6 \cdot H_2O$) (Sigma Aldrich) and 10% HCl and a reaction was allowed to occur for 30 minutes for staining. After washing three times with a phosphate buffer solution, the cells were stained with nuclear fast red (TCI) for 5 minutes, and washed again three times with a phosphate buffer solution. The washed cells were sequentially dehydrated using 10%, 90%, and 100% alcohol, and then treated with mounting medium and observed under a microscope. The results thereof are shown in FIG. 8.

Figure 8:
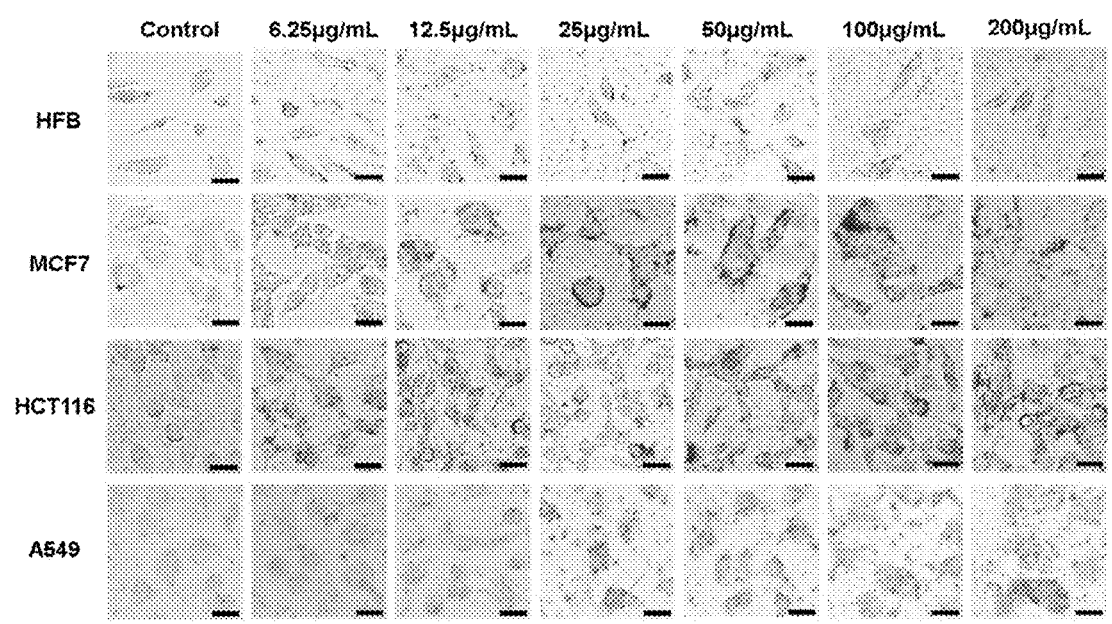
FIG. 8 illustrates the results of confirming whether iron particles of iron/hyaluronic acid nanoparticles according to an embodiment of the present disclosure migrate into cells by Prussian blue staining.

As shown in FIG. 8, it was confirmed that, in the case of cancer cells, the amount of nanoparticles introduced into the cells was significantly increased according to the concentration of nanoparticles when treated with the FHA NPs, and the shape of the cells was not maintained such that a large number of cells whose cell membranes were broken by lipid peroxidation and cells whose forms were destroyed were observed. In contrast, it was confirmed that, in the case of normal cells, when treated with a high concentration of the FHA NPs, the nanoparticles could be partially introduced into the cells, but the shape of the cells was maintained the same. This was confirmed to be due to the fact that, in the case of normal cells, even though the FHA NPs were introduced into the cells, the expression of a receptor for releasing iron to the outside is normally operated, and thus the FHA NPs introduced into the cells are normally released to the outside, thus not inducing ferroptosis. From the above results, it was confirmed that the FHA NPs according to the present disclosure induced cancer cell-specific ferroptosis to induce the death of cancer cells.

Example 7

Confirmation of Anticancer Effect of FHA NPs 7.1. Confirmation of Tumor Growth Inhibitory Effect of FHA NPs To determine whether the FHA NPs exhibit a tumor growth inhibitory effect in vivo, primary tumor animal models were prepared. More specifically, 4- to 5-week-old male sterile Balb/c mice (Dooyeol Biotech, Inc.) were purchased, were allowed to drink/eat adequate water and food, and subjected to an adaptation period in which the conditions of 25±1° C. and 12 hour light/dark cycles were maintained. Then, $2.5 \times 10^6$ of A549 cells, which are a human lung cancer cell line, were subcutaneously injected into the left and right legs of each mouse, and then when the tumor size reached 450 mm$^3$, the FHA NPs were injected into each mouse at a concentration of 8 mg/kg every 24 hours using a peritumoral injection method, and the volume size was measured at intervals of 2 days or 3 days. For tumor size measurement, the length and width of tumors were measured using a caliper and substituted into the following equation, and a phosphate buffer solution was used as a control instead of the FHA NPs and injected in the same manner as described above. All animal studies were conducted in accordance with the Institutional Animal Care and Use Committee (IACUC) guidelines. The results thereof are shown in FIG. 9.

$$V = \frac{Width^2 \times Length}{2}$$

Figure 9:
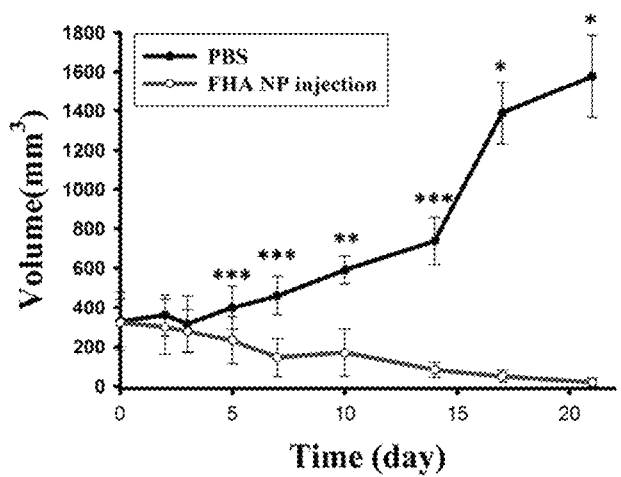
FIG. 9 illustrates the results of measuring a change in tumor volume according to treatment with iron/hyaluronic acid nanoparticles according to an embodiment of the present disclosure, wherein * denotes $P<0.05$,  denotes $P<0.01$, * denotes $P<0.001$.

As illustrated in FIG. 9, it was confirmed that the control injected with a phosphate buffer solution exhibited a significant increase in tumor size to 1500±210 mm$^3$ over time, whereas the tumor size was gradually reduced and significantly reduced to the size of 32±23 mm$^3$ in the case of the experimental group treated with the FHA NPs.

In addition, some of the mice on which the same experiment was conducted were euthanized at 0 hours, 12 hours, 24 hours, day 3, day 7, day 14, and day 21, and then tumors were obtained therefrom and the weights of the tumors were measured. The results thereof are shown in FIG. 10.

Figure 10A:
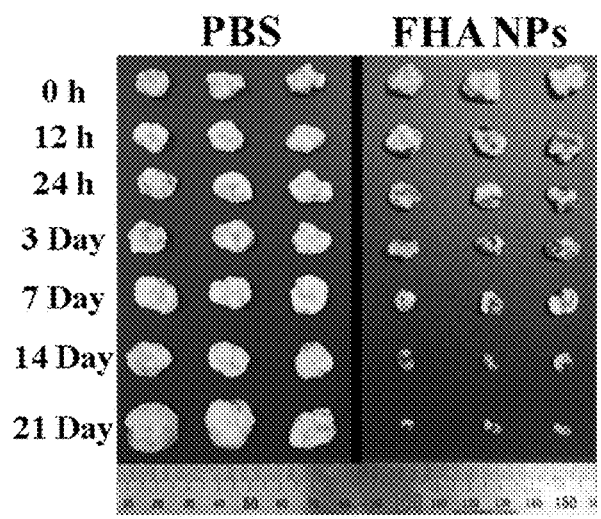
FIG. 10A illustrates the results of photographing changes in tumor volume according to treatment with iron/hyaluronic acid nanoparticles according to an embodiment of the present disclosure.
Figure 10B:
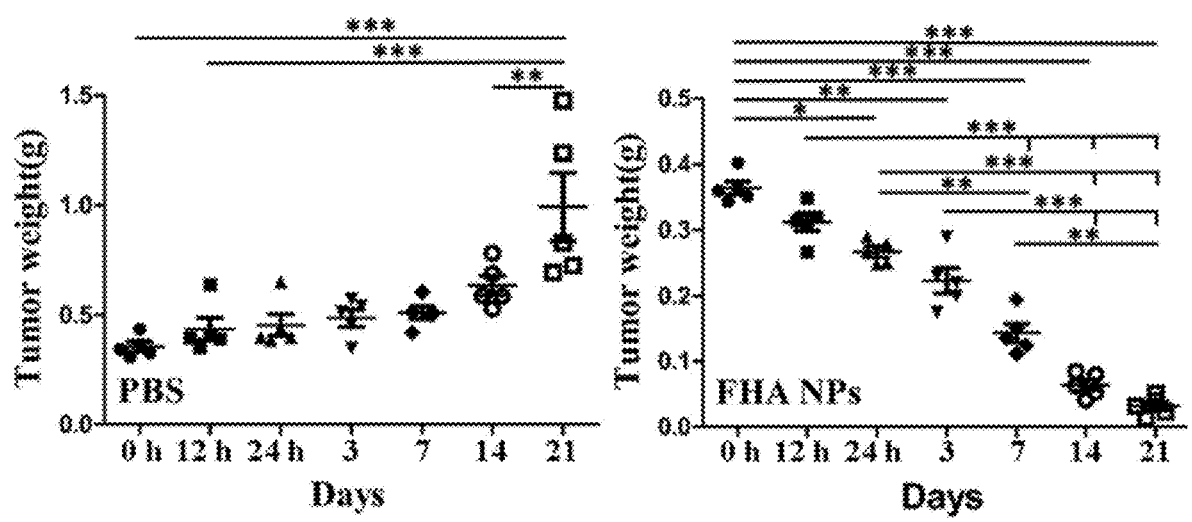
FIG. 10B illustrates the results of measuring the weights of acquired tumors, wherein * denotes $P<0.05$,  denotes $P<0.01$, * denotes $P<0.001$.

As illustrated in FIG. 10, it was confirmed that the control into which a phosphate buffer solution was injected exhibited an increase in tumor weight from 0.35 g to 1.4 g, whereas the experimental group into which the FHA NPs were injected exhibited a significant decrease in tumor weight from 0.35 g to 0.03 g.

From the above results, it was confirmed that the FHA NPs according to the present disclosure not only effectively inhibited tumor growth in vivo, but also exhibited a tumor therapeutic effect through cancer cell death.

7.2. Confirmation of Accumulation of FHA NPs in Cancer Tissue

It was examined by MRI whether the FHA NPs were normally accumulated only in cancer tissue in vivo. More specifically, the FHA NPs were injected into tumor animal models produced in the same manner as in Example 7.1 at a concentration of 8 mg/kg every 24 hours using a peritumoral injection method, and after 14 days, all tumors and normal tissues of the heart, spleen, liver, kidneys, and lungs were observed by MRI. MRI was performed using a Bruker Biospec 7T system (BioSpec 70/20 USR) using a 35 mm quadrature coil, and scanning parameters were identified as TR=200 ms, TE=10 ms, and a slice thickness of 1 mm. The results thereof are shown in FIG. 11.

Figure 11:
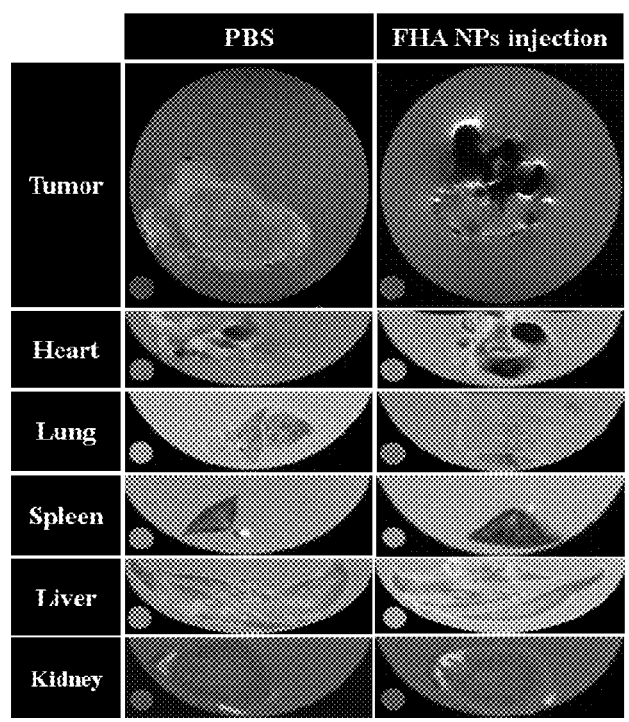
FIG. 11 illustrates the results of confirming the accumulation of iron/hyaluronic acid nanoparticles according to an embodiment of the present disclosure in cancer cells by MRI.

As illustrated in FIG. 11, it was confirmed that, while no iron particles were observed in the heart, spleen, liver, kidneys, and lungs, a high concentration of iron particles were observed in tumor tissues of the experimental group into which the FHA NPs were injected. From the above results, it was confirmed that the FHA NPs according to the present disclosure did not affect other organs and exhibited a cancer tissue-specific effect.

7.3. Confirmation of Cancer Cell Killing Effect in Tumor Tissue of FHA NPs

To determine whether the FHA NPs exhibit a cancer cell killing effect in tumor tissue in vivo, histological analysis was performed. More specifically, tumor tissue obtained in the same manner as in Example 7.1 was fixed with 3.7% formaldehyde for 12 hours and stained by H&E staining. The results thereof are shown in FIG. 12.

Figure 12:
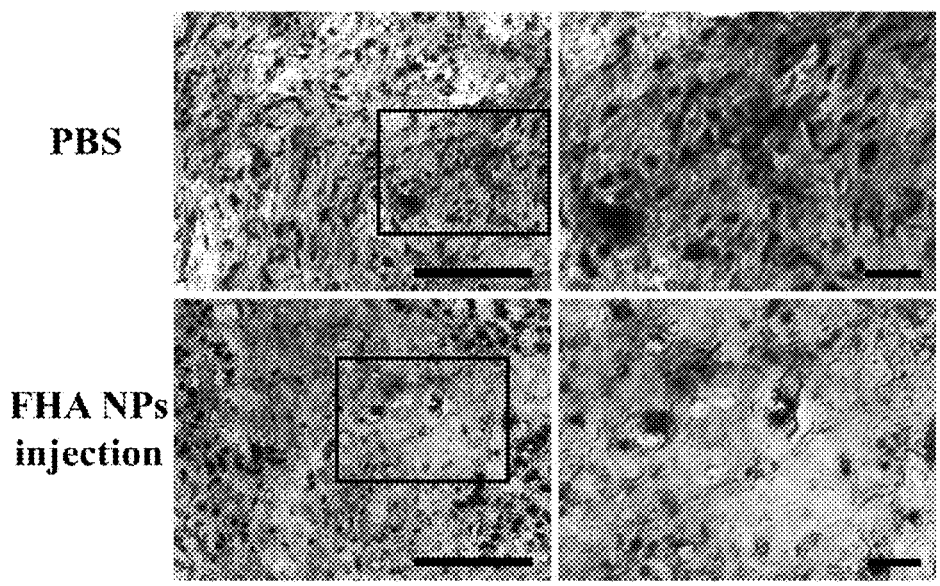
FIG. 12 illustrates the results of confirming the cancer cell killing effect of iron/hyaluronic acid nanoparticles according to an embodiment of the present disclosure by H&E staining, wherein scale bars indicate 50 μm, and the right views are enlarged views of box portions shown in the left views.

As illustrated in FIG. 12, it was confirmed that, while no cell death was induced in the control into which a phosphate buffer solution was injected, and thus the nuclei of tumors was uniformly distributed, cell death was induced in tumor tissues of the experimental group into which the FHA NPs were injected and thus the number of nuclei was significantly reduced. From the above results, it was confirmed that the FHA NPs according to the present disclosure effectively exhibited a cancer cell killing effect in tumor tissue even in vivo.

From the above results, it was confirmed that the FHA NPs according to the present disclosure had a structure in which iron particles of Fe$_3$O$_4$ were uniformly bound to hyaluronic acid nanoparticles having an average diameter of 100 nm, and had excellent stability, thus enabling long-term stable storage. In addition, the FHA NPs do not affect normal cells or normal tissues, and are selectively accumulated in cells of cancer tissue to increase the concentration of iron particles in cancer cells and ROS, thereby inducing the selective death of cancer cells through ferroptosis, and thus exhibit a high cancer therapeutic effect due to less side effects, and accordingly, are expected to be effectively used for the treatment of various cancers.

As is apparent from the foregoing description, iron/hydrogel nanoparticles according to the present disclosure are harmless components included in the body, and are prepared only using iron and hydrogel particles without additional components, and thus can be stably used without toxicity. In addition, the iron/hydrogel nanoparticles of the present disclosure can be prepared using a simple method, and thus not only can be mass-produced, but also have high stability and thus enable long-term stable storage without aggregation, and accordingly, are a pharmaceutically superior preparation. In addition, the iron/hydrogel nanoparticles according to the present disclosure are specifically accumulated in cancer cells of cancer tissue, and the nanoparticles accumulated in cancer cells effectively induce cancer cell death through ferroptosis, and thus are expected to exhibit less side effects and high therapeutic effects in the treatment of various cancers.

The foregoing description of the present disclosure is provided for illustrative purposes only, and it will be understood by those of ordinary skill in the art to which the present disclosure pertains that the present disclosure may be easily modified into other particular forms without changing the technical spirit or essential characteristics of the present disclosure. Thus, the above-described embodiments should be construed as being provided for illustrative purposes only and not for purposes of limitation.

What is claimed is:

1. A method of treating cancer comprising administering a pharmaceutical composition comprising an active ingredient to a subject in need thereof, wherein the active ingredient is nanoparticles comprising iron and a cancer cell-targeting hydrogel wherein the nanoparticles are in a form in which an iron cation and an anion of the cancer cell-targeting hydrogel are bound and aggregated, wherein the cancer cell-targeting hydrogel selectively binds to a CD44 receptor on surfaces of cancer cells, wherein the nanoparticles themselves are active ingredient to treat the cancer, and wherein the nanoparticles do not contain additional components including a stabilizer and polyethyleneimine (PEI).

2. The method of claim 1, wherein the cancer cell-targeting hydrogel is hyaluronic acid.

3. The method of claim 1, wherein the nanoparticles have a diameter of about 50 nm to about 200 nm.

4. The method of claim 1, wherein the nanoparticles induce cancer cell death through ferroptosis.

5. The method of claim 1, wherein the cancer comprises any one or more selected from the group consisting of breast cancer, colorectal cancer, rectal cancer, lung cancer, colon cancer, thyroid cancer, oral cancer, pharyngeal cancer, laryngeal cancer, cervical cancer, brain cancer, ovarian cancer, bladder cancer, kidney cancer, liver cancer, pancreatic cancer, prostate cancer, skin cancer, tongue cancer, uterine cancer, gastric cancer, bone cancer, and blood cancer.

* * * * *

SEQUENCE LISTING

```
<160> NUMBER OF SEQ ID NOS: 8

<210> SEQ ID NO 1
<211> LENGTH: 21
<212> TYPE: DNA
<213> ORGANISM: Artificial Sequence
<220> FEATURE:
<223> OTHER INFORMATION: Bax Forward Primer

<400> SEQUENCE: 1
aggcggcggg cccaccagct c                                              21

<210> SEQ ID NO 2
<211> LENGTH: 21
<212> TYPE: DNA
<213> ORGANISM: Artificial Sequence
<220> FEATURE:
<223> OTHER INFORMATION: Bax Reverse Primer

<400> SEQUENCE: 2
catcagcaaa catgtcagct g                                              21

<210> SEQ ID NO 3
<211> LENGTH: 22
<212> TYPE: DNA
<213> ORGANISM: Artificial Sequence
<220> FEATURE:
<223> OTHER INFORMATION: Ripk1 Forward Primer

<400> SEQUENCE: 3
ggcattgaag aaaaatttag gc                                             22

<210> SEQ ID NO 4
<211> LENGTH: 21
<212> TYPE: DNA
<213> ORGANISM: Artificial Sequence
<220> FEATURE:
<223> OTHER INFORMATION: Ripk1 Reverse Primer

<400> SEQUENCE: 4
tcacaactgc attttcgttt g                                              21

<210> SEQ ID NO 5
<211> LENGTH: 22
<212> TYPE: DNA
<213> ORGANISM: Artificial Sequence
<220> FEATURE:
<223> OTHER INFORMATION: GPX4 Forward Primer

<400> SEQUENCE: 5
acaagaacgg ctgcgtggtg aa                                             22

<210> SEQ ID NO 6
<211> LENGTH: 22
<212> TYPE: DNA
```

```
<213> ORGANISM: Artificial Sequence
<220> FEATURE:
<223> OTHER INFORMATION: GPX4 Reverse Primer

<400> SEQUENCE: 6
gccacacact tgtggagcta ga                                        22

<210> SEQ ID NO 7
<211> LENGTH: 21
<212> TYPE: DNA
<213> ORGANISM: Artificial Sequence
<220> FEATURE:
<223> OTHER INFORMATION: Beta-actin Forward Primer

<400> SEQUENCE: 7
gtgggccgct ctaggcacca a                                         21

<210> SEQ ID NO 8
<211> LENGTH: 24
<212> TYPE: DNA
<213> ORGANISM: Artificial Sequence
<220> FEATURE:
<223> OTHER INFORMATION: Beta-actin Reverse Primer

<400> SEQUENCE: 8
ctttagcacg cactgtagtt tctc                                      24
```